(12) United States Patent
Ahlheim et al.

(10) Patent No.: US 8,815,293 B2
(45) Date of Patent: *Aug. 26, 2014

(54) ORGANIC COMPOUNDS

(75) Inventors: Markus Ahlheim, Staufen (DE); Rolf Loeffler, Freiburg (DE)

(73) Assignee: Novartis AG, Basel (CH)

( * ) Notice: Subject to any disclaimer, the term of this patent is extended or adjusted under 35 U.S.C. 154(b) by 252 days.

This patent is subject to a terminal disclaimer.

(21) Appl. No.: 12/784,251

(22) Filed: May 20, 2010

(65) Prior Publication Data

US 2010/0233217 A1 Sep. 16, 2010

Related U.S. Application Data

(63) Continuation of application No. 10/283,989, filed on Oct. 30, 2002, now Pat. No. 7,767,230.

(60) Provisional application No. 60/339,036, filed on Oct. 30, 2001.

(51) Int. Cl.
*A61K 9/14* (2006.01)
*A61K 31/454* (2006.01)

(52) U.S. Cl.
USPC ............ 424/489; 424/469; 424/482; 514/321

(58) Field of Classification Search
CPC ............ A61K 31/454; A61K 2300/00; A61K 9/0024; A61K 9/14; A61K 47/10
See application file for complete search history.

(56) References Cited

U.S. PATENT DOCUMENTS

| | | | |
|---|---|---|---|
| 4,780,460 A | 10/1988 | Dusterlerg et al. | |
| 5,364,866 A | 11/1994 | Strupczewski et al. | |
| 5,460,956 A | 10/1995 | Reichert et al. | |
| 5,538,739 A | 7/1996 | Bodmer et al. | |
| 5,741,485 A | 4/1998 | Reichert et al. | |
| 5,776,963 A | 7/1998 | Strupczewski et al. | |
| 5,955,459 A | 9/1999 | Bradley et al. | |
| 6,368,632 B1 | 4/2002 | Mesens et al. | |
| 6,555,544 B2 | 4/2003 | Francois et al. | |
| 7,767,230 B2 * | 8/2010 | Ahlheim et al. .............. | 424/489 |
| 2002/0045582 A1 | 4/2002 | Margolin et al. | |

FOREIGN PATENT DOCUMENTS

| | | | |
|---|---|---|---|
| CA | 2327883 | A1 | 10/1999 |
| CN | 1137756 | A | 12/1996 |
| EP | 0307619 | A2 | 3/1989 |
| EP | 0402644 | A1 | 12/1990 |
| GB | 2145422 | A | 3/1985 |
| JP | 60-76531 | A | 5/1985 |
| JP | 9-505286 | | 5/1997 |
| JP | 9-511215 | | 11/1997 |
| WO | 9513814 | A1 | 5/1995 |
| WO | 9854186 | A1 | 12/1998 |
| WO | 0023057 | A2 | 4/2000 |
| WO | 0192334 | A1 | 12/2001 |
| WO | 03020707 | A1 | 3/2003 |
| WO | 2004006886 | A2 | 1/2004 |

OTHER PUBLICATIONS

Kelleher, J.P. et al., "Advances in Atypical Antipsychotics for the Treatment of Schizophrenia—New Formulations and New Agents," CNS Drugs, ADIS International, Auckland, NZ, vol. 16, No. 4, pp. 249-161 (2000).
Mucke, H.A.M. et al., "Iloperidone," Drugs of the Future, Prous Science, Barcelona, ES, vol. 25, No. 1, pp. 29-40 (2000).
Hesselink, Jan M. Keppel, Current Opinion in Central & Peripheral Nervous System Investigational Drugs 2(1) pp. 71-78 (2000), Abstract Only.
Kongsamut, Sathapana, et al. Iloperidone binding to human and rat dopamine and 5-HT receptors, Eur. J. Pharmacol. 317 (1996) pp. 417-423.
Canadian Intellectual Property Office, Examiner's Report dated Jan. 18, 2011, Canadian Application No. 2,463,158, 2 pgs.
European Patent Office, Extended European Search Report dated Jan. 27, 2011, EP Application No. 10009932.4-2123, 9 pgs.
Borst, PCT/EP02/12073/, International Search Report, Jun. 3, 2003, 9 pages.
PCT/EP02/12073, Written Opinion, May 23, 2003, 2 pages.
Senkel, H., PCT/EP02/12073, International Preliminary Examination Report, Feb. 6, 2004, 6 pages.
Brazil Patent Application No. PI0213564-7, Office Action 1 Letter, Mar. 17, 2011, 2 pages.
Canadian Patent Application No. 2,463,158, Office Action 1, Mar. 10, 2009, 2 pages.
Canadian Patent Application No. 2,463,158, Office Action 2, Apr. 12, 2010, 2 pages.
Chinese Patent Application No. 02821426.9, Office Action 1, Jun. 24, 2005, 6 pages.
Chinese Patent Application No. 02821426.9, Office Action 2, Sep. 21, 2007, 3 pages.
Chinese Patent Application No. 02821426.9, Office Action 3, Jan. 18, 2008, 4 pages.
Chinese Patent Application No. 02821426.9, Rejection Decision, Jan. 21, 2009, 4 pages.
Chinese Patent Application No. 02821426.9, Panel Decision, Jan. 12, 2010, 7 pages.
Chinese Patent Application No. 02821426.9, Reexamination Decision, Jan. 29, 2010, 18 pages.
Chinese Patent Application No. 201010269414.6, Office Action 1, Mar. 22, 2011, 32 pages.
European Patent Application No. 02785330.8, Examination Report, Nov. 3, 2006, 5 pages.
European Patent Application No. 02785330.8, Examination Report, Aug. 12, 2008, 4 pages.
European Patent Application No. 02785330.8, Rejection, Oral Proceeding Summons, Jul. 30, 2009, 6 pages.
European Patent Application No. 02785330.8, Oral Proceeding Minutes, May 28, 2010, 14 pages.

*Primary Examiner* — Lakshmi Channavajjala
(74) *Attorney, Agent, or Firm* — Hoffman Warnick LLC; Drew Holmes

(57) ABSTRACT

A depot formulation comprising iloperidone and a biodegradable, biocompatible polymer. Preferably, the polymer is a star polymer.

22 Claims, No Drawings

(56) References Cited

OTHER PUBLICATIONS

European Patent Application No. 02785330.8, Intention to Grant, Jun. 9, 2010, 16 pages.
Japanese Patent Application No. 2003-539681, Office Action 1 Letter, Feb. 24, 2009, 1 page.
Japanese Patent Application No. 2003-539681, Final Office Action Letter, Nov. 4, 2009, 1 page.
Yebassa, U.S. Appl. No. 10/283,989, Office Action, Jun. 13, 2005, 43 pages.
Yebassa, U.S. Appl. No. 10/283,989, Final Office Action, Mar. 7, 2006, 8 pages.
Yebassa, U.S. Appl. No. 10/283,989, Office Action, Jun. 11, 2007, 27 pages.
Corbett et al., "Effects of Atypical Antipsychotic Agents on Social Behavior in Rodents," 1993, Pharmacology Biochemistry and Behavior, vol. 45, pp. 9-17.
U.S. Appl. No. 10/283,989, Declaration of Curt Wolfgang, Ph.D., Under 37 CFR 1.132, Nov. 8, 2007, 24 pages.
U.S. Appl. No. 10/283,989, Final Office Action, Feb. 11, 2008, 9 pages.
U.S. Appl. No. 10/283,989, Office Action, Sep. 9, 2008, 12 pages.
U.S. Appl. No. 10/283,989, Declaration of Deepak S. Phadke, Ph.D., Under 37 CFR 1.132, Jan. 9, 2009, 11 pages.
U.S. Appl. No. 10/283,989, Office Action, Apr. 16, 2009, 13 pages.
U.S. Appl. No. 10/283,989, Declaration of Dr. James W. McGinity, Under 37 CFR 1.132, Sep. 25, 2009, 41 pages.
U.S. Appl. No. 10/283,989, Declaration of Dr. Steven G. Potkin, Under 37 CFR 1.132, Sep. 29, 2009, 11 pages.
U.S. Appl. No. 10/283,989, Interview Summary, Sep. 30, 2009, 4 pages.
U.S. Appl. No. 10/283,989, Notice of Allowance & Fees Due, Feb. 23, 2010, 13 pages.
M. Horioka, Injection, Nanzando, pp. 23-25 (1995).
Miescher et al., Depot Effect of crystal suspensions of female sex hormones (Ovocyclin—and Lutocyclin [progesterone]—crystal ampoules), Helv. Physiol. Acta 2, 515-532.
Mutlib et al., "Picogram determination of iloperidone in human plasma by solid-phase extraction and by high-performance liquid chromatography-selected-ion monitoring electrospray mass spectrometry", Journal of Chromatography B, 1995, 237-246.
Corey et al., "A Stable and Easily Prepared Catalyst for the Enantioselective Reduction of Ketones. Applications to Multistep Syntheses", J. Am. Chem. Soc. 1987, 109, 7925-7926.
T. Okano, New Pharmacy, 3rd Ed., pp. 76-81 (1987).
Pieters et al., "Sustained Release Properties of an Intra-adiposely Administered Dapsone Depot Injection," International Journal of Leprosy, vol. 54, No. 3 (Sep. 9, 2007), pp. 383-388.
Schilffarth, "About the symptomatic treatment of hay fever with a new depot crystal suspension," Therapie der Gegenwart 117 (1978), pp. 797-807 (English translation version).
Blagden et al., "Crystal engineering of active pharmaceutical ingredients to improve solubility and dissolution rates," Advanced Drug Delivery Reviews 59 (May 2007), pp. 617-630.
Shekunov et al., "Crystallization processes in pharmaceutical technology and drug delivery design," Journal of Crystal Growth 211 (2000), pp. 122-136.
Vippagunta et al., "Crystalline solids," Advanced Drug Delivery Reviews 48 (2001), pp. 3-26.
Rodriguez-Spong et al., "General principles of pharmaceutical solid polymorphism: a supramolecular perspective," Advanced Drug Delivery Reviews 56 (2004), pp. 241-274.
Singhal et al., "Drug polymorphism and dosage form design: a practical perspective," Advanced Drug Delivery Reviews 56 (2004), pp. 335-347.
Rothele et al., "Standards in Laser Diffraction," Proc. 5th European Symposium Particle Characterization, Mar. 1992, pp. 625-642.
Heuer et al., "Results Obtained with a New Instrument for the Measurement of Particle Size Distributions from Diffraction Patterns," Oct. 1984, Part. Charact. 2, pp. 7-13.

* cited by examiner

ORGANIC COMPOUNDS

CROSS REFERENCE TO RELATED APPLICATIONS

The current application is a continuation application of co-pending U.S. patent application Ser. No. 10/283,989, filed on Oct. 30, 2002, which claims priority to U.S. Provisional Patent Application Ser. No. 60/339,036, filed on Oct. 30, 2001, both of which are hereby incorporated by reference.

This present invention relates to pharmaceutical compositions, in particular to depot formulations comprising iloperidone as active agent and a biodegradable, biocompatible star polymer, as well as a process for preparing microparticle depot formulations.

Iloperidone is 1-[4-[3-[4-(6-fluoro-1,2-benzisoxazol-3-yl)-1-piperidinyl]propoxy]-3-methoxyphenyl]ethanone. As used herein, "iloperidone" includes any pharmaceutically acceptable salts, hydrates, solvates, and/or stereoisomers thereof, and any metabolites thereof, including any salts, hydrates, solvates and/or stereoisomers of such metabolites.

U.S. Pat. No. 5,364,866 describes the compound iloperidone useful as an anti-psychotic and analgesic agent. U.S. Pat. No. 5,955,459 describes compositions for treating schizophrenia containing conjugates of a fatty acid and iloperidone.

The present inventors have found that depot formulations comprising iloperidone entrapped in a biodegradable, biocompatible polymer, preferably a star polymer, e.g., poly(d,l-lactide-co-glycolide). Accordingly the present invention provides with such depot formulations a controlled-release of iloperidone over, e.g., 2-6 weeks.

The depot formulations of the present invention comprising iloperidone and a biodegradable, biocompatible star polymer may be in the form of microparticles.

As used herein, "biocompatible" means that the polymer is not toxic to the human body, is pharmaceutically acceptable, and is not carcinogenic. As used herein, "biodegradable" means a material that should degrade by bodily processes to products readily disposable by the body and should not accumulate in the body.

Suitable polymers, e.g., star polymers, used by the present invention are typically branched polyesters. As used herein "star polymer" is understood to mean that the structure of the polyester is star-shaped. These polyesters have a single polyol residue as a central moiety surrounded by acid residue chains. The polyol moiety may be, e.g., glucose or, e.g., mannitol. These esters are known and described in GB 2,145,422 and in U.S. Pat. No. 5,538,739.

The star polymers may be prepared using polyhydroxy compounds, e.g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. Typically 0.2% glucose is used to initiate polymerization. The branched polyesters, e.g., poly(d,l-lactide-co-glycolide) have a central glucose moiety having rays of linear polylactide chains. The preferred polyester chains in the star polymer compounds preferably used according to the invention are co-polymers of the alpha carboxylic acid moieties, lactic acid and glycolic acid, or of the lactone dimers. The molar ratio of lactide:glycolide may be from about 75:25 to 25:75, e.g., 60:40 to 40:60, with from 55:45 to 45:55, e.g., 55:45 to 50:50 more preferred.

The branched polyesters, e.g., poly(d,l-lactide-co-glycolide) having a central glucose moiety having rays of linear polylactide chains preferably have an average molecular weight $M_n$ in the range of from about 10,000 to 200,000 Daltons, preferably 25,000 to 100,000 Daltons, especially 35,000 to 60,000 Daltons and a polydispersity, e.g., of from 1.7 to 3.0, e.g., 2.0 to 2.5. The intrinsic viscosities of star polymers of $M_n$ 35,000 and $M_n$ 60,000 are 0.36 and 0.51 dl/g, respectively, in chloroform. A star polymer having a $M_n$ 52,000 has a viscosity of 0.475 dl/g in chloroform.

The terms microsphere, microcapsule and microparticle are considered to be interchangeable with respect to the invention, and denote the encapsulation of the active agent by the polymer, preferably with the active agent distributed throughout the polymer, which is then a matrix for the active agent. In that case preferably the terms microsphere or more generally microparticle are used.

The amount of iloperidone incorporated in the implants or microparticles is from about 1 to about 90 weight percent, based on the total weight of the implant or microparticle. Preferably, the amount of iloperidone incorporated in the implants or microparticles is from 50 to 80 weight percent, more preferably 60 to 75 weight percent.

In one embodiment of this invention, the microparticles contain further excipients such as surfactants or solvents, e.g., solid solvents. Such excipients may accelerate or further retard the release of the active agent.

The components of the compositions of the invention may be described in Fiedler, H. P. "Lexikon der Hilfsstoffe für Pharmazie, Kosmetik und angrenzende Gebiete", Editio Cantor Verlag Aulendorf, Aulendorf, 4th revised and expanded edition (1996), the contents of which are hereby incorporated by reference.

The microparticles of the current invention are usually made up of particles of a spherical shape, although microparticles may be irregularly shaped. They may exhibit a smooth to rough surface and can be dense or porous like. The microparticles have an average particle size from 3 to 300 microns, preferably from 10 to 200 microns.

According to another aspect the invention provides a process for preparing microparticles comprising iloperidone or a pharmaceutically acceptable salt thereof and a biodegradable, biocompatible star polymer. The microparticles may be manufactured by several processes, e.g., coacervation, e.g., spray drying or, e.g., solvent evaporation. Solvent evaporation is a preferred process, which comprises the following steps:

i) dissolving the polymer and iloperidone in an organic solvent, e.g., methylene chloride,
ii) mixing an aqueous solution of a surfactant, e.g., polyvinyl alcohol, and a buffer, e.g., disodium hydrogen phosphate,
iii) mixing the solution of step i) and step ii) using a static mixer to form an emulsion,
iv) optionally heating the emulsion to an elevated temperature, e.g., between about 30 to about 60° C., preferably between 40° C. and 50° C.,
v) collecting the generated microparticles by sedimentation,
vi) optionally washing the microparticles, and
vii) drying the microparticles under vacuum.

The ratio of the solutions i) and ii) combined in step iii) may be from 1:20 to 5:1, preferably from 1:20 to 1:5.

A variety of solvents may be used for the internal phase such as halogenated and/or aliphatic or aromatic hydrocarbons as well as mixtures of those with a water miscible liquid. Preferably the solvent is methylene chloride.

As surfactants in the external phase may be used poly(vinyl alcohol), carboxymethyl cellulose, gelatin, poly(vinyl pyrrolidone), polyoxyethylene 20 sorbitan monooleate and polyoxyethylene 20 sorbitan monolaurate.

The microparticles of the present invention are useful for the treatment of central nervous system disorders, e.g., psychotic disorders, e.g., schizophrenia, or, e.g., as analgesics.

The depot formulations of microparticles of the invention may be administered by intramuscular or subcutaneous injection. Depot formulations of this invention administered by injection provide an effective treatment of diseases over an extended period, e.g., over 2 to 6 weeks. The microparticles allow a controlled release of iloperidone by diffusion and therefore steady-state levels of the drug are obtained over the extended period.

The exact amount of active agent entrapped in the polymer, i.e., the exact amount of depot formulation, e.g., microparticles formulation, to be administered depends on a number of factors, e.g., the condition to be treated, the desired duration of treatment, the rate of release of active agent and the degradability of the polymeric matrix. The amount of active agent required may be determined on the basis of known in vitro or in vivo techniques. Repeated administration of the depot formulation of the invention may be effected when the drug is sufficiently released.

Dosages required in practicing the method of the present invention will vary depending upon, e.g., the mode of administration and the severity of the condition to be treated. Large amount of active agent, e.g., up to 360 mg of active agent, e.g., in form of a suspension, may be administered in a single administration, e.g., in one injection.

Microparticles prepared by the process of the present invention are stored in the form of a powder. For administration as injection the microparticles are suspended in a suitable vehicle.

Filling may be effected before or after sterilization of the depot formulation. Sterilization of the formulation of the present invention and the primary package can be effected, e.g., by gamma irradiation, e.g., at an energy of 25 kGy, without degradation of active agent and/or microparticles.

Following is a description by way of example only of depot formulations of this invention.

EXAMPLES 1 TO 4

Microparticles with Drug Loadings 20 to 75 Weight Percent

|  | Ex. 1 Drug loading 20% | Ex. 2 Drug loading 30% | Ex. 3 Drug loading 60% | Ex. 4 Drug loading 75% |
|---|---|---|---|---|
| Internal phase | | | | |
| Iloperidone | 1.6 g | 90 g | 7 g | 67.5 g |
| poly(d,l,-lactide-co-glycolide) | 6.4 g | 210 g | 4.8 g | 22.5 g |
| $CH_2Cl_2$ | 21.3 ml | 630 ml | 30 ml | 144 ml |
| External phase | | | | |
| polyvinyl alcohol | 25 g | 119.7 g | — | 25 g |
| $Na_2HPO_4$ | 4.7 g | 75.5 g | — | 47.3 g |
| Water for injection | 1 l | 8 l | — | 5 l |
| Solution in vessel | | | | |
| polyvinyl alcohol | — | 337.5 g | 150 g | 425 g |
| $Na_2HPO_4$ | — | 213 g | 28.4 g | 268 g |
| Water for injection | — | 68 l | 6 l | 85 l |
| Static mixer | DN2, 20 Elements | DN6, 14 Elements | — | DN6, 14 Elements |

The internal phase is prepared by dissolving lloperidone and the poly(d,l,-lactide-co-glycolide) in methylene chloride. A polyvinyl alcohol in water solution with disodium hydrogen phosphate ($Na_2HPO_4$) is prepared (external phase).

The resulting solutions (internal phase and external phase) are filtered and pumped through a static mixer into a stirred vessel containing a solution of polyvinyl alcohol and disodium hydrogen phosphate in water. The resulting solution is heated to 40° C.-50° C. with stirring within 90 min. After cooling the suspension is allowed to sediment for 20 min. The aqueous solution of polyvinyl is reduced under vacuo. Optionally the microparticles are re-suspended again in aqueous disodium hydrogen phosphate solution and treated as above (heating, cooling, sedimentation, removal of the supernatant). The microparticles are washed with water for approximately 30 min. After sedimentation for 20 min, the solution is removed and the microparticles are filtered through an Ultipor filter, washed with water and dried under vacuum.

The examples provide iloperidone microparticles with drug loading up to 80% by weight. The high drug loading allows fewer injections with a long-lasting effect.

What is claimed is:

1. An intramuscular or subcutaneous depot formulation comprising iloperidone and a biodegradable, biocompatible polymer,
    wherein the depot formulation is in the form of microparticles,
    wherein the formulation includes from 50 percent to 90 percent iloperidone by weight,
    wherein the formulation, following a single intramuscular or subcutaneous injection, provides an effective treatment amount of iloperidone over a period of over about 2 weeks and up to about 6 weeks, and
    wherein the polymer is a polylactide-co-glycolide.

2. The intramuscular or subcutaneous depot formulation of claim 1, wherein the amount of iloperidone is from 50 to about 80 weight percent.

3. The intramuscular or subcutaneous depot formulation of claim 1, wherein the microparticles have an average particle size of about 10 to about 200 microns.

4. The intramuscular or subcutaneous depot formulation of claim 2, wherein the amount of iloperidone is from about 60 to about 75 weight percent.

5. The intramuscular or subcutaneous depot formulation of claim 1, wherein the molar ratio of lactide to glycolide is from about 40:60 to about 60:40.

6. The intramuscular or subcutaneous depot formulation of claim 1, wherein the polymer is a star polymer comprising a polylactide-co-glycolide ester of a polyol.

7. The intramuscular or subcutaneous depot formulation of claim 6 wherein the polyol contains at least 3 hydroxy groups and has a molecular weight of up to about 20,000 Daltons.

8. The intramuscular or subcutaneous depot formulation of claim 7 wherein the microparticles have an average particle size of about 10 to about 200 microns.

9. The intramuscular or subcutaneous depot formulation of claim 8 wherein the polylactide-co-glycolide polymer chains have an average molecular weight of about 25,000 to about 100,000 Daltons.

10. The intramuscular or subcutaneous depot formulation of claim 9 wherein the formulation contains up to about 360 mg of iloperidone.

11. The intramuscular or subcutaneous depot formulation of claim 4, wherein the polymer is a polylactide-co-glycolide, and wherein the molar ratio of lactide to glycolide is from about 40:60 to about 60:40.

12. The intramuscular or subcutaneous depot formulation of claim 4, wherein the polymer is a star polymer comprising a polylactide-co-glycolide ester of a polyol.

13. The intramuscular or subcutaneous depot formulation of claim 12 wherein the polyol contains at least 3 hydroxy groups and has a molecular weight of up to about 20,000 Daltons.

14. The intramuscular or subcutaneous depot formulation of claim 13 wherein the microparticles have an average particle size of about 10 to about 200 microns.

15. The intramuscular or subcutaneous depot formulation of claim 14 wherein the polylactide-co-glycolide polymer chains have an average molecular weight of about 25,000 to about 100,000 Daltons.

16. The intramuscular or subcutaneous depot formulation of claim 15 wherein the formulation contains up to about 360 mg of iloperidone.

17. An intramuscular or subcutaneous depot formulation comprising iloperidone and a biodegradable, biocompatible polymer,
wherein the depot formulation is in the form of microparticles,
wherein the formulation, following intramuscular or subcutaneous injection, provides an effective treatment amount of iloperidone over a period of over about 2 weeks and up to about 6 weeks, wherein:
the polymer is a polylactide-co-glycolide;
the amount of iloperidone is from about 50 to about 90 weight percent;
the microparticles have an average particle size of about 10 to about 200 microns;
the molar ratio of lactide to glycolide is from about 40:60 to about 60:40;
the polyol contains at least 3 hydroxy groups and has a molecular weight of up to about 20,000 Daltons; and
the polylactide-co-glycolide polymer chains have an average molecular weight of about 25,000 to about 100,000 Daltons.

18. The depot formulation of claim 17, wherein:
the amount of iloperidone is from about 60 to about 75 weight percent;
the molar ratio of lactide to glycolide is from about 55:45 to about 45:50;
wherein the polymer is a star polymer comprising a polylactide-co-glycolide ester of a polyol;
the polyol contains at least 3 hydroxy groups and has a molecular weight of up to about 20,000 Daltons.

19. The depot formulation of claim 18, wherein the polyol is glucose.

20. The depot formulation of claim 17, wherein:
the amount of iloperidone is from about 60 to about 75 weight percent; and
the molar ratio of lactide to glycolide is from about 55:45 to about 45:50.

21. A process for preparing an intramuscular or subcutaneous depot formulation comprising iloperidone and a biodegradable, biocompatible polyactide-co-glycolide polymer,
wherein the formulation, following intramuscular or subcutaneous injection, provides an effective treatment amount of iloperidone over a period of over about 2 weeks and up to about 6 weeks, wherein the formulation includes from 50 percent to 90 percent iloperidone by weight,
said process comprising preparing microparticles by:
i) dissolving the polyactide-co-glycolide polymer and iloperidone in an organic solvent,
ii) preparing an aqueous solution of a surfactant and optionally a buffer,
iii) mixing the solution obtained in step i) and the solution obtained in step ii) to form an emulsion,
iv) removing the organic solvent to obtain said microparticles comprising iloperidone and the biodegradable, biocompatible polyactide-co-glycolide polymer in an aqueous solution,
v) collecting said microparticles by sedimentation or filtration,
vi) optionally washing the microparticles, and
vii) drying the microparticles.

22. A method of treating a central nervous system disorder comprising intramuscularly or subcutaneously administering the depot formulation according to any of claim 1 or claim 17 by administering a single injection per treatment period of over about 2 weeks to about 6 weeks.

* * * * *